US008467916B2

(12) United States Patent
Narasimhulu et al.

(10) Patent No.: US 8,467,916 B2
(45) Date of Patent: *Jun. 18, 2013

(54) SYSTEM AND METHOD FOR COMPUTING AN EQUI-TIME POINT FOR AIRCRAFTS

(75) Inventors: Veeresh Kumar Masaru Narasimhulu, Bangalore (IN); Dinesh Kumar Kushwaha, Bangalore (IN)

(73) Assignee: Airbus Engineering Centre India, Bangalore, Karnataka (IN)

( * ) Notice: Subject to any disclaimer, the term of this patent is extended or adjusted under 35 U.S.C. 154(b) by 0 days.

This patent is subject to a terminal disclaimer.

(21) Appl. No.: 13/382,289

(22) PCT Filed: Jul. 19, 2010

(86) PCT No.: PCT/IN2010/000480
§ 371 (c)(1),
(2), (4) Date: Jan. 5, 2012

(87) PCT Pub. No.: WO2011/027358
PCT Pub. Date: Mar. 10, 2011

(65) Prior Publication Data
US 2012/0123616 A1    May 17, 2012

(30) Foreign Application Priority Data
Jul. 24, 2009   (IN) .......................... 1752/CHE/2009

(51) Int. Cl.
*G06F 17/00*    (2006.01)
(52) U.S. Cl.
USPC ............... 701/3; 701/120; 701/122; 701/123; 701/301; 701/411; 701/467; 701/528; 701/532; 701/533; 244/175; 244/186; 340/945; 455/66.1; 455/98

(58) Field of Classification Search
USPC .............. 701/3, 4, 8, 10, 11, 13, 15, 16, 120, 701/122, 123, 301, 411, 467, 528, 532, 533; 244/76 R, 175, 186; 340/945; 455/66.1, 98
See application file for complete search history.

(56) References Cited

U.S. PATENT DOCUMENTS

| 5,270,931 | A  | * | 12/1993 | Appleford ........................ 701/3 |
| 6,965,816 | B2 | * | 11/2005 | Walker ............................ 701/16 |
| 2008/0300739 | A1 | * | 12/2008 | Coulmeau et al. ................ 701/8 |
| 2009/0076721 | A1 | * | 3/2009 | Coulmeau et al. ............ 701/206 |
| 2009/0082955 | A1 | * | 3/2009 | Sacle et al. .................... 701/206 |
| 2010/0152996 | A1 | * | 6/2010 | Blanchon et al. ............. 701/120 |
| 2012/0109428 | A1 | * | 5/2012 | Narasimhulu et al. .......... 701/16 |
| 2012/0130564 | A1 | * | 5/2012 | Narasimhulu et al. ............ 701/3 |

* cited by examiner

*Primary Examiner* — James Trammell
*Assistant Examiner* — McDieunel Marc
(74) *Attorney, Agent, or Firm* — Prakash Nama; Global IP Services, PLLC (57) ABSTRACT

A method of a flight management system (FMS) of an aircraft for generating an equi-time point (ETP) for an emergency landing of the aircraft includes receiving at least two reference points for landing the aircraft upon an occurrence of an emergency. The method also includes determining an equi-distance point (EDP) for the aircraft by locating a first point on the remaining flight path of the aircraft which is equidistant from the at least two reference points. The method further includes generating an ETP for the aircraft by locating a second point on the remaining flight path such that time difference between any two of expected flight times of the aircraft from the second point to the at least two reference points is less than a threshold value.

20 Claims, 9 Drawing Sheets

SYSTEM AND METHOD FOR COMPUTING AN EQUI-TIME POINT FOR AIRCRAFTS

FIELD OF TECHNOLOGY

The present invention relates to the field of aeronautical engineering. In particular, the present invention relates to a flight management system (FMS).

BACKGROUND

A flight management system (FMS) is a fundamental part of an aircraft which is used to control a navigation of the aircraft. The FMS may hold a flight plan of the aircraft, and allow the pilot to modify the flight plan as required during the flight. The FMS uses various sensors to determine a position of the aircraft. Given the position and the flight plan, the FMS may guide the aircraft along the flight plan or a flight path. The FMS is normally controlled through a small screen and a keyboard. The FMS also may display the flight plan on an electronic flight instrument system (EFIS), navigation display (ND) or multi-function display (MFD). Further, the FMS may compute predicted speed, altitude, fuel consumed along the flight plan, and so on.

An equi-time point (ETP) may be computed by the FMS to safely navigate the aircraft, where the ETP may provide a point from which the time to fly to a first reference point (e.g., a first airport) is substantially equal to the time to fly to a second reference point (e.g., a second airport). Accordingly, the ETP may act as an advisory for the pilot during emergency situations where an emergency landing may be required. Currently, publicly visible methods for computing such a point appear to use a simplified formula based on many approximations. Further, the method seems to assume the flight to each reference point as a constant speed flight, where the wind factor, aircraft characteristics, and other flight related factors may be ignored. Thus, there may be room for an error in determining the ETP.

SUMMARY

A system and method for computing an equi-time point (ETP) for aircrafts is disclosed. In one aspect, a method of a flight management system (FMS) of an aircraft for generating an ETP for an emergency landing of the aircraft includes receiving at least two reference points for landing the aircraft upon an occurrence of an emergency. The method also includes determining an equi-distance point (EDP) for the aircraft by locating a first point on the remaining flight path of the aircraft which is equidistant from the at least two reference points. Then, the method includes generating an ETP for the aircraft by locating a second point on the remaining flight path of the aircraft such that a time difference between any two of expected flight times of the aircraft from the second point to the at least two reference points is less than a threshold value, where an approximation of the second point is initially based on the EDP.

In another aspect, an article includes a storage medium having instructions, that when executed by a computing platform of an FMS of an aircraft, result in execution of the method described above.

In yet another aspect, a system of an FMS of an aircraft for generating an ETP for an emergency landing of the aircraft includes a processor, and a memory coupled to the processor. The memory is configured for storing a set of instructions, that when executed by the processor, causes the processor to perform the method described above.

The methods, systems and apparatuses disclosed herein may be implemented in any means for achieving various aspects, and other features will be apparent from the accompanying drawings and from the detailed description that follow.

BRIEF DESCRIPTION OF THE DRAWINGS

Various preferred embodiments are described herein with reference to the drawings, wherein.

The drawings described herein are for illustration purposes only and are not intended to limit the scope of the present disclosure in any way.

DETAILED DESCRIPTION

A system and method for computing an equi-time point (ETP) for aircrafts is disclosed. In the following detailed description of the embodiments of the invention, reference is made to the accompanying drawings that form a part hereof, and in which are shown by way of illustration specific embodiments in which the invention may be practiced. These embodiments are described in sufficient detail to enable those skilled in the art to practice the invention, and it is to be understood that other embodiments may be utilized and that changes may be made without departing from the scope of the present invention. The following detailed description is, therefore, not to be taken in a limiting sense, and the scope of the present invention is defined only by the appended claims. It is appreciated that the terms 'expected flight time' and 'flight time' are used interchangeably throughout the document.

Figure 1:
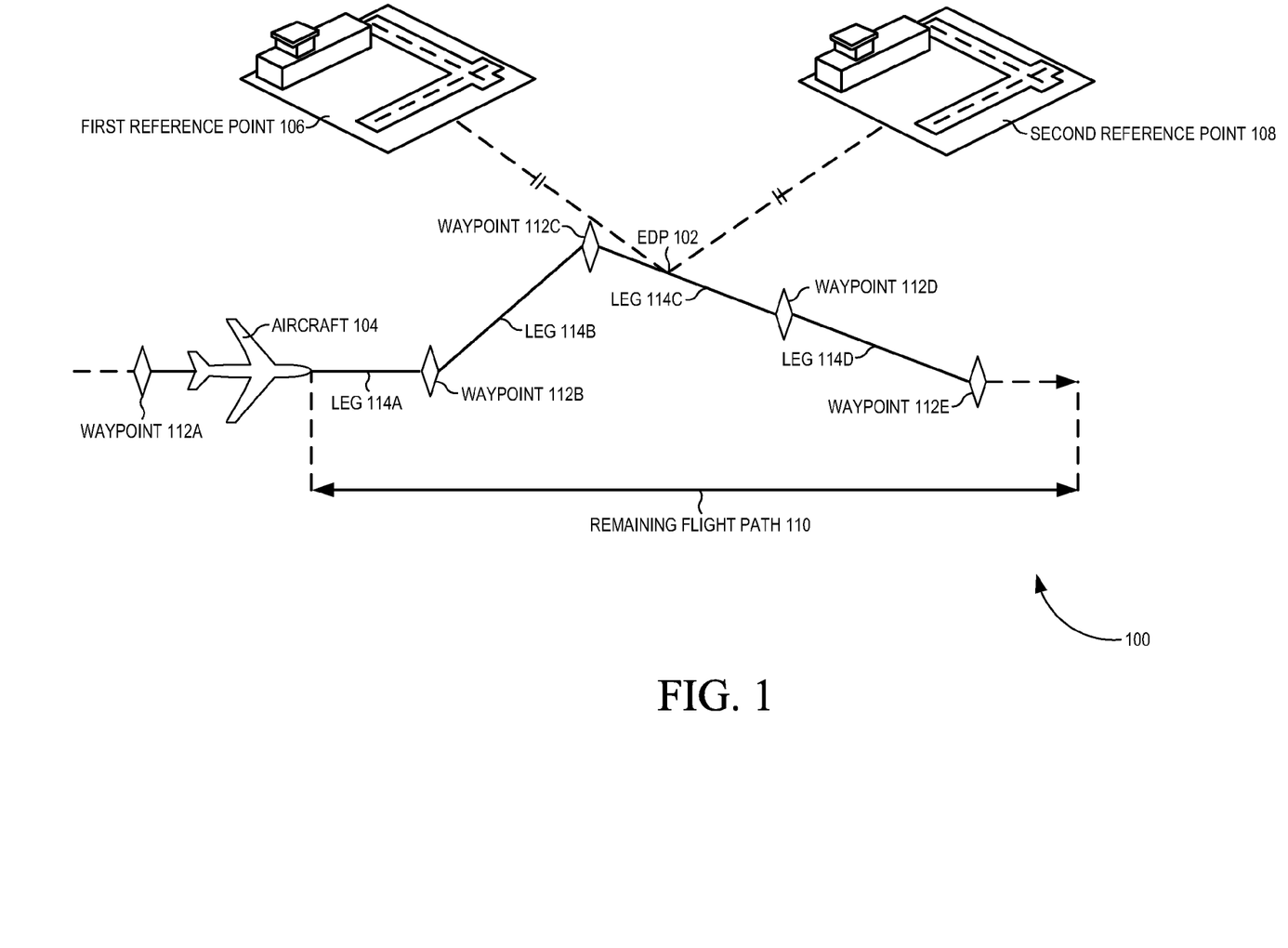
FIG. 1 illustrates an exemplary schematic representation illustrating generation of an equi-distance point (EDP) for an aircraft, according to an embodiment of the invention.

FIG. 1 illustrates an exemplary schematic representation 100 illustrating generation of an EDP 102 for an aircraft 104, according to an embodiment of the invention. In particular, FIG. 1 shows a flight plan serviced by a flight management system (FMS) of the aircraft 104. The flight plan includes a plurality of waypoints 112A-E and a plurality of legs 114A-D. The waypoints 112A-E may be a set of coordinates (e.g., latitudinal and longitudinal coordinates) in physical space. The plurality of legs 114A-D represents a flight path of the aircraft 104.

According to an embodiment of the present invention, a first reference point 106 and a second reference point 108 are received by the FMS of the aircraft 104 for landing the aircraft 104 upon the occurrence of an emergency. In one embodiment, the first reference point 106 and the second reference point 108 may be entered by a pilot of the aircraft 104 based on a current location of the aircraft 104. In an alternate embodiment, the first reference point 106 and the second reference point 108 may be automatically selected by the FMS based on the current location of the aircraft 104.

The first reference point 106 and the second reference point 108 may be a departure airport and an arrival airport for the aircraft 104 by default. Alternatively, each of the first reference point 106 and the second reference point 108 may be an airport (other than the departure airport and the arrival airport), an airdrome, an airstrip, a runway, a landing field, an airfield and the like which is proximal to the current location of the aircraft 104. In one embodiment, more than two reference points can also be received from the pilot or automatically selected based on the current location of the aircraft 104.

Further, a remaining flight path 110 of the aircraft 104 is determined based on the current location of the aircraft 104 and the flight plan. The EDP 102 is then generated by locating a point on the remaining flight path 110 (e.g., on any of the plurality of legs 114B-D) which is equidistant from the first reference point 106 and the second reference point 108.

Figure 2:
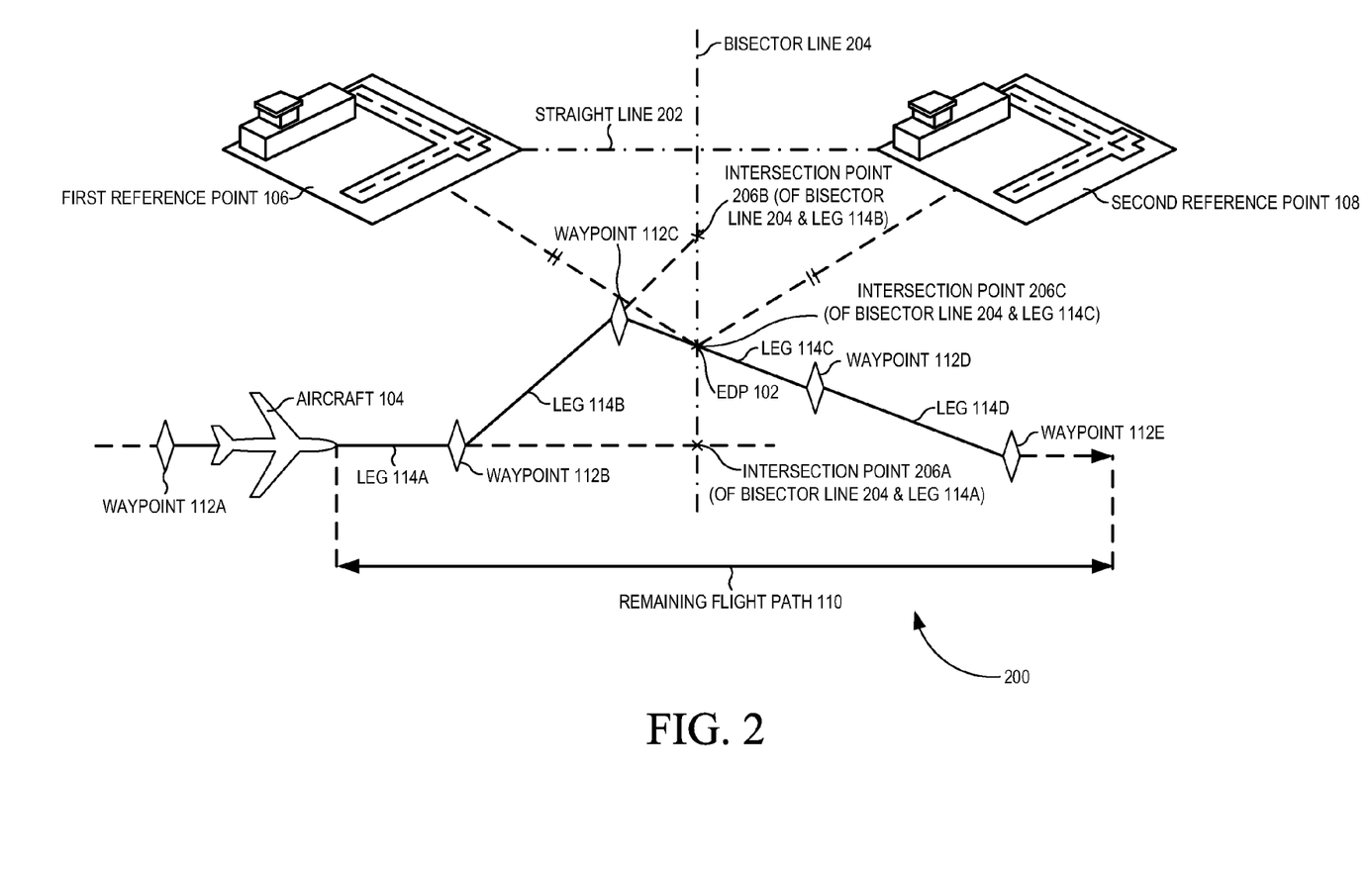
FIG. 2 illustrates an exemplary schematic representation illustrating computation of the EDP for the aircraft of FIG. 1 with respect to the remaining flight path, according to an embodiment of the invention.

FIG. 2 illustrates an exemplary schematic representation 200 illustrating computation of the EDP 102 for the aircraft 104 from FIG. 1 with respect to the remaining flight path 110, according to an embodiment of the invention. As discussed above, the EDP 102 is computed by locating a point on the remaining flight path 110 of the aircraft 104. For computing the EDP 102, a straight line 202 is formed between the first reference point 106 and the second reference point 108. The straight line 202 is formed using a first equation $Y_{ref}=M_{ref}X_{ref}+C_{ref}$ in Cartesian coordinates. The Cartesian coordinates include an X-axis and a Y-axis for defining a position of the aircraft 104. For example, the X-axis represents a longitudinal line at 0° and the Y-axis represents a latitudinal line at 0°. The slope ($M_{ref}$) of the straight line 202 is computed using the equation:

$$M_{ref} = \frac{Y_{ref2} - Y_{ref1}}{X_{ref2} - X_{ref1}},$$

where $X_{ref1}$ and $Y_{ref1}$ refer to longitude and latitude of the first reference point 106 and $X_{ref2}$ and $Y_{ref2}$ refer to longitude and latitude of the second reference point 108. Further, the intercept ($C_{ref}$) of a reference Y-axis for the straight line 202 is computed using $C_{ref}=Y_{ref2}-M_{ref}X_{ref2}$.

Then, a bisector line 204 is generated and extended perpendicular to the straight line 202. The bisector line 204 is generated using a second equation $Y_{perp}=M_{perp}X_{perp}+C_{perp}$ with $$M_{perp} = \frac{-1}{M_{ref}}$$

being a slope of the bisector line 204 and $$C_{perp} = \frac{Y_{ref1} + Y_{ref2}}{2} + \frac{1}{M_{ref}}\left(\frac{X_{ref1} + X_{ref2}}{2}\right)$$

being an intercept of the reference Y-axis.

Further, intersection points of the bisector line 204 with the plurality of legs 114A-D in the remaining flight path 110 are located. In one embodiment, each of the plurality of legs 114A-D is based on a third equation $Y_{wpt}=M_{wpt}X_{wpt}+C_{wpt}$ in Cartesian coordinates with $$M_{wpt} = \frac{Y_{wpt2} - Y_{wpt1}}{X_{wpt2} - X_{wpt1}}$$

being the slope of the each of the plurality of legs 114A-D and $C_{wpt}=Y_{wpt2}-M_{wpt}X_{wpt2}$ being the intercept of the reference Y-axis. In the above equations for $M_{wpt}$ and $C_{wpt}$, $X_{wpt1}$ and $Y_{wpt1}$ refers to longitudinal and latitudinal coordinates of a first or start waypoint of each of the legs 114A-D and $X_{wpt2}$ and $Y_{wpt2}$ refers to longitudinal and latitudinal coordinates of a second or end waypoint of each of the legs 114A-D.

As illustrated, the bisector line 204 intersects the leg 114A at an intersection point 206A. Also, the bisector line 204 intersects the leg 114B at an intersection point 206B. Similarly, the bisector line 204 intersects the leg 114C at an intersection point 206C. Although it is not illustrated in FIG. 2, there can be more intersection points as there are more legs in the remaining flight path 110. Based on the intersection points 206A-C, the EDP 102 for the aircraft 104 is computed. In one embodiment, the EDP 102 for the aircraft 104 is computed by comparing a length of each of the plurality of legs 114A-C with a distance between a start point of each of the plurality of legs 114A-C and the corresponding intersection point. According to an embodiment of the present invention, an intersection point of a leg and the bisector line 204 is determined as the EDP 102 if the length of the leg is greater than the distance between the start point of the leg and the intersection point.

In the example embodiment illustrated in FIG. 2, the length of the leg 114B is compared with the distance between the start point of the leg 114B and the intersection point 206B. It can be seen from FIG. 2 that, the length of the leg 114B is less than the distance between the start point of the leg 114B and the intersection point 206B. Thus, the intersection point 206B is determined to be not the EDP 102. Further, the length of the leg 114C is compared with the distance between the start of the leg 114C and the intersection point 206C. It can be seen from FIG. 2 that, the length of the leg 114C is greater than the distance between the start point of the leg 114C and the intersection point 206C. Hence, the intersection point 206C is determined as the EDP 102.

Figure 3:
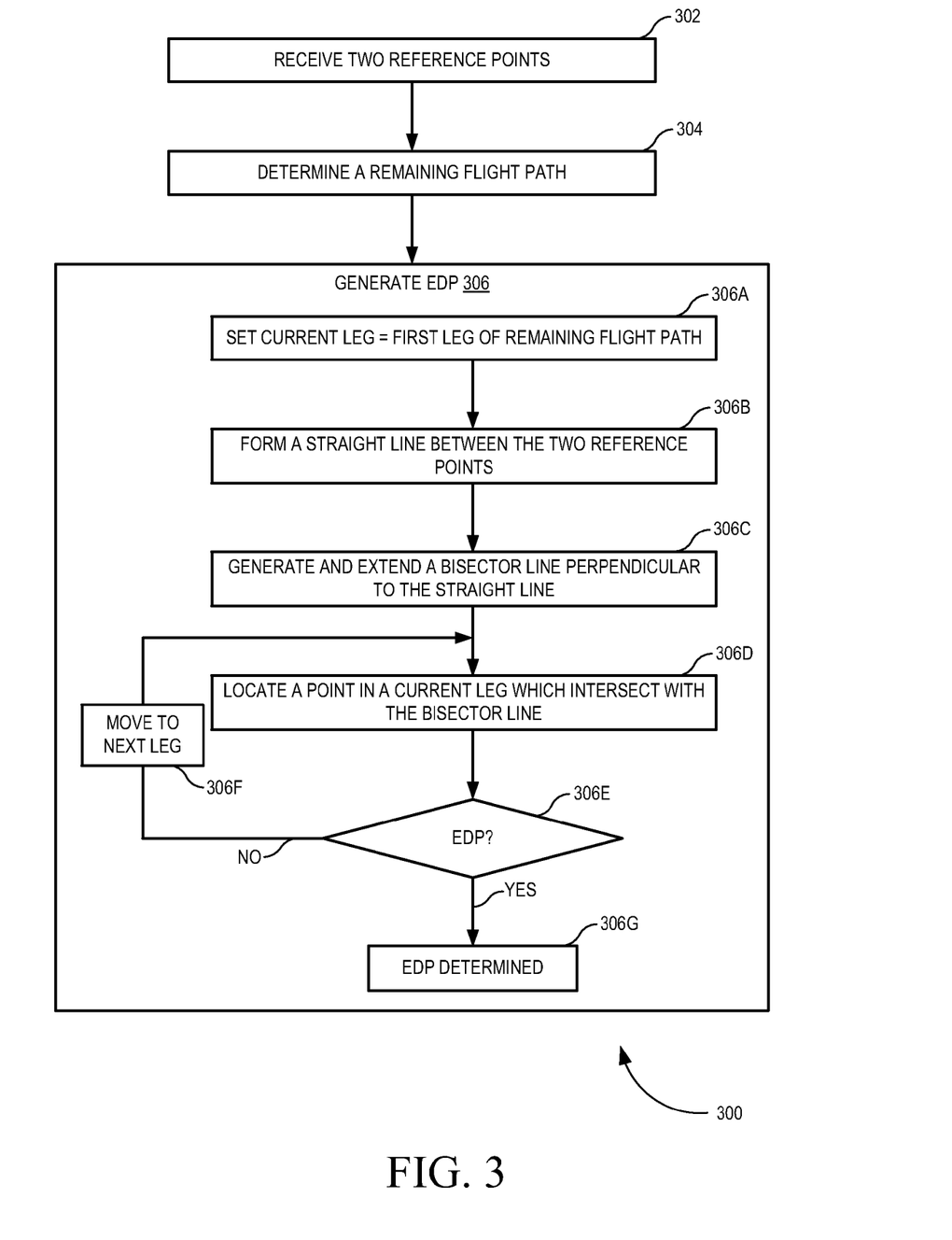
FIG. 3 illustrates a process flowchart of an exemplary method of a flight management system (FMS) of an aircraft for dynamically computing an EDP for the aircraft, according to an embodiment of the invention.

FIG. 3 illustrates a process flowchart of an exemplary method 300 of an FMS of an aircraft for dynamically computing an EDP for the aircraft, according to an embodiment of the invention. In step 302, two reference points for landing the aircraft are received. For example, the two reference points may be received from a pilot of the aircraft or may be automatically chosen, upon an occurrence of an emergency. In step 304, a remaining flight path for the aircraft is determined. The determination may be based on a current location of the aircraft and a flight plan serviced by the FMS of the aircraft.

The method 300 then performs step 306 in which the EDP for the aircraft is computed. In one embodiment, the EDP is computed by locating a point in the remaining flight path which is equidistant from the two reference points. The remaining flight path includes a plurality of way points and a plurality of legs. Moreover, the steps involved in computing the EDP are described in steps 306A through 306G. In step 306A, a first leg of the remaining flight path is set as a current leg. In step 306B, a straight line is formed between the two reference points. In step 306C, a bisector line is generated and extended perpendicular to the straight line.

In step 306D, a point in the current leg which intersects the bisector line is located. In step 306E, it is determined whether the intersection point is the EDP. The step is carried out by comparing the length of the current leg with the distance between the start point of the current leg and the intersection point. If the length of the current leg is greater than the distance between the start point of the current leg and the intersection point, then the intersection point is determined as the EDP in step 306G.

If the length of the current leg is less than the distance between the start point of the current leg and the intersection point, then the next leg in the remaining flight path is selected as the current leg in step 306F. Further, the step 306D is repeated to locate a point in the next leg which intersects with the bisector line. It is appreciated that steps 306E, 306F and 306G may be repeated until the EDP is determined. It is also appreciated that the steps 306A-G may use mathematical formulas described in FIG. 2 to obtain the EDP.

Figure 4:
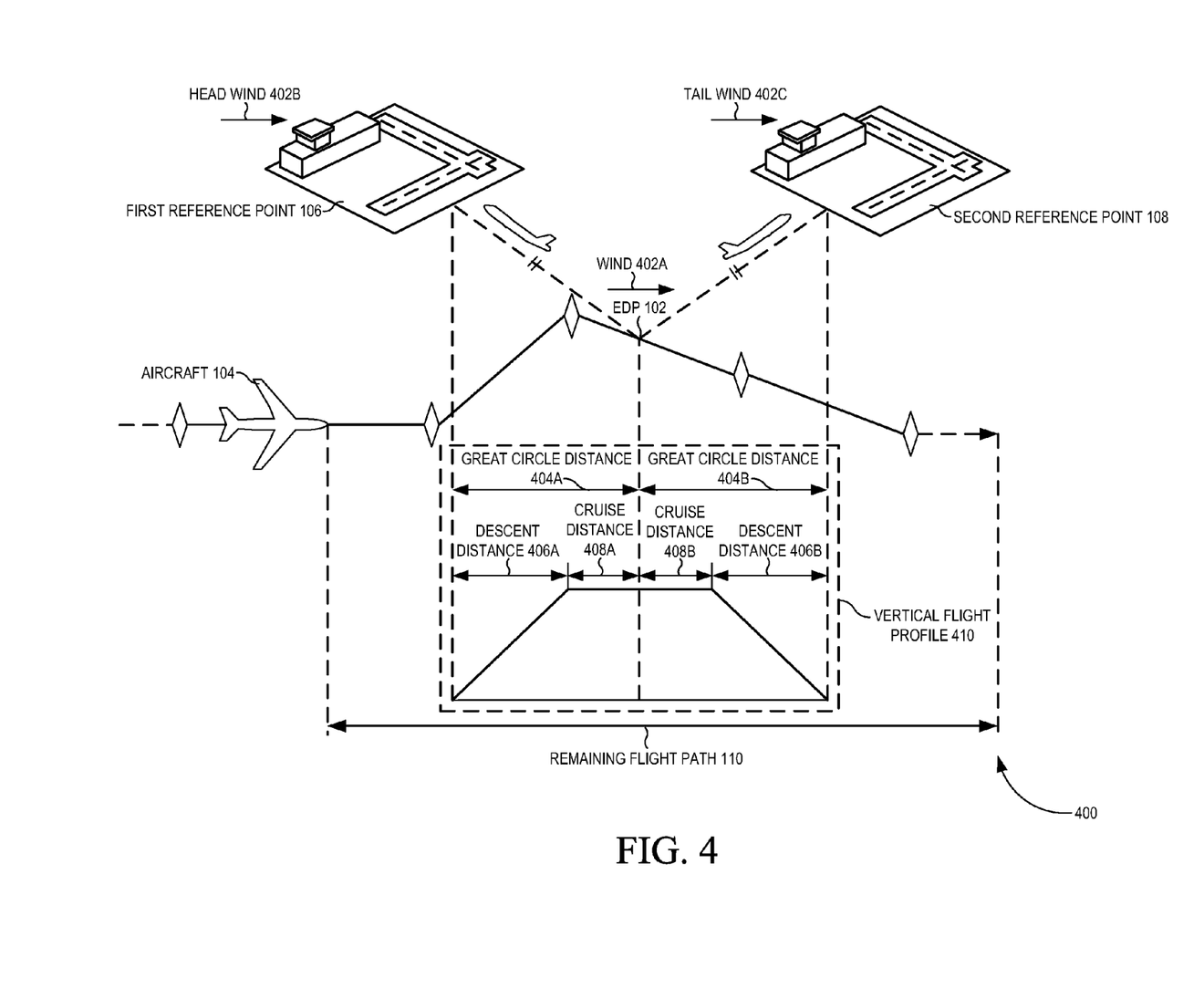
FIG. 4 illustrates an exemplary schematic representation illustrating computation of flight time from the EDP to each reference point, according to an embodiment of the invention.

FIG. 4 illustrates an exemplary schematic representation 400 illustrating computation of flight time from the EDP 102 to each reference point (e.g., the first reference point 106 and the second reference point 108), according to an embodiment of the invention. In one embodiment, the flight time from the EDP 102 to the first reference point 106 and the second reference point 108 is calculated by the FMS for emergency landing of the aircraft 104. In this embodiment, the flight time of the aircraft 104 from the EDP 102 to the first reference point 106 and the second reference point 108 is calculated based on factors effecting the flight time of the aircraft 104. Exemplary factors affecting the flight time of the aircraft 104 may include a wind velocity at the first reference point 106 and the second reference point 108 (e.g., determined based on a head wind 402B and a tail wind 402C), characteristics of the aircraft 104 (e.g., a type, a performance level, a condition, etc. of the aircraft 104) and/or a distance from the EDP 102 to the first reference point 106 and the second reference point 108.

As illustrated, the flight time of the aircraft 104 from the EDP 102 to the first reference point 106 and the second reference point 108 is calculated based on a default flight profile (e.g., a vertical flight profile 410) flying a great circle distance 404A or 404B. The great circle distance 404A or 404B is the shortest distance between the EDP 102 and the first reference point 106 or the second reference point 108, respectively. As can be seen from FIG. 4, the great circle distance 404A is a sum of a cruise distance 406A and a descent distance 408A. Also, the great circle distance 404B is a sum of a cruise distance 406B and a descent distance 408B.

According to an embodiment of the present invention, the flight time from the EDP 102 to the first reference point 106 is a sum of a cruise time for the cruise distance 406A and a descent time for the descent distance 408A. The cruise time for the cruise distance 406A is calculated as:

cruise time=cruise distance/ground speed, where, the ground speed is a sum of a true air speed (TAS) and a wind velocity at a cruise altitude. In one exemplary implementation, the cruise time is calculated based on an assumption that an expected cruise flight of the aircraft 104 for the cruise distance 406A is carried out at an optimum speed (e.g., in mach) based on a predicted gross weight of the aircraft 104 and an effect of wind 402A at the EDP 102. The TAS is calculated by converting the optimum speed to a true air speed at cruise conditions.

The descent time for the descent distance 408A is calculated by taking into account allowances stored in a performance database of the aircraft 104. In one example embodiment, the descent time is a sum of allowances at different altitudes that are stored in the performance database for a particular descent distance. It is appreciated that the allowances refer to aircraft performance data, such as time, distance, fuel etc. associated with the flight of the aircraft 104. It is further appreciated that the allowances may be stored in tables, where the tables are used to interpolate respective time, distance, fuel, etc. as functions of the gross weight and altitude of the aircraft 104. These tables may also be based on simplified algorithms for a default profile of the aircraft 104 in the case of an emergency. For example, the allowances in the tables may be used to account to engine failure of the aircraft 104. In case of the engine failure, the corresponding tables are used to reflect its effect on the descent time taken by the aircraft 104. The descent time for the descent distance 408A is also calculated based on a wind velocity (e.g., the head wind 402B) at the first reference point 106.

Similarly, the flight time from the EDP 102 to the second reference point 108 is a sum of a cruise time for the cruise distance 406B and a descent time for the descent distance 408B. The cruise time for the cruise distance 406B is calculated as:

cruise time=cruise distance/ground speed, where, the ground speed is a sum of a true air speed (TAS) and a wind velocity at a cruise altitude. In one exemplary implementation, the cruise time is calculated based on an assumption that an expected cruise flight of the aircraft 104 for the cruise distance 406B is carried out at an optimum speed based on a predicted gross weight of the aircraft 104 and an effect of wind 402A at the EDP 102. The TAS is calculated by converting the optimum speed to a true air speed at cruise conditions.

The descent time for the descent distance 408B is calculated by taking into account allowances stored in a performance database of the aircraft 104. In one example embodiment, the descent time is a sum of allowances at different altitudes that are stored in the performance database for a particular descent distance. The descent time for the descent distance 408B is also calculated based on a wind velocity (e.g., the tail wind 402C) at the second reference point 108. Thus, in the manner described above, the FMS of the aircraft 104 computes the flight time of the aircraft 104 from the EDP 102 to the first reference point 106 and to the second reference point 108.

Figure 5:
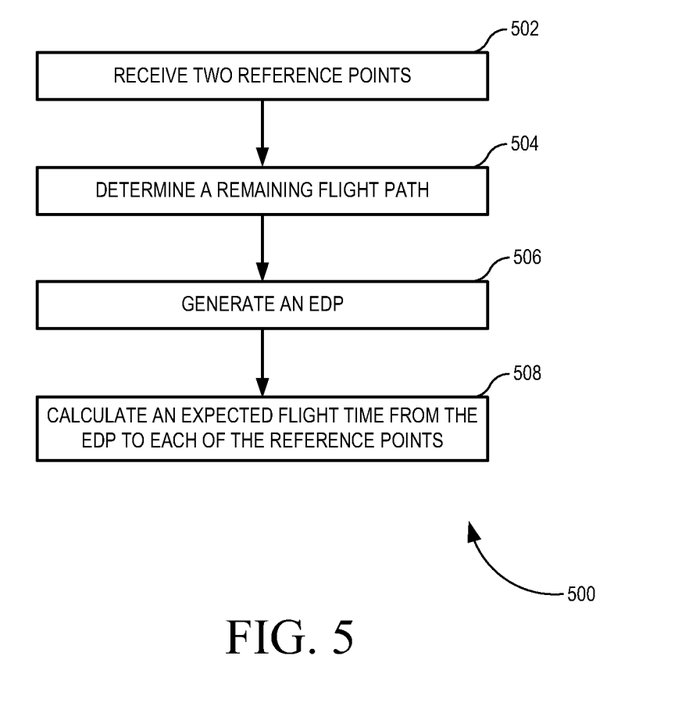
FIG. 5 illustrates a process flowchart of an exemplary method of an FMS of an aircraft for computing flight time from the EDP to each reference point, according to an embodiment of the invention.

FIG. 5 illustrates a process flowchart of an exemplary method 500 of an FMS of an aircraft for computing flight time from an EDP to each reference point, according to an embodiment of the invention. In step 502, two reference points are received from a pilot of the aircraft for landing the aircraft upon an occurrence of an emergency. In step 504, a remaining flight path is determined based on a current location of the aircraft and a flight plan serviced by the FMS. In step 506, the EDP for the aircraft is generated by locating a point in the remaining flight path which is equidistant from the two reference points.

In step 508, an expected flight time of the aircraft from the EDP to each of the two reference points is calculated based on a plurality of factors affecting the flight time of the aircraft. For example, the plurality of factors affecting the flight time includes a wind velocity, characteristics of the aircraft, and/or a distance from the EDP to the each one of the two reference points. Further, the expected flight time of the aircraft is calculated based on a default flight profile flying a great circle distance. The great circle distance includes a cruise distance and a descent distance of the aircraft from the EDP to the each one of the two reference points.

In one exemplary implementation, the flight time from the EDP to the each of the two reference points is a sum of a descent time for the descent distance and a cruise time for the cruise distance. The descent time for the descent distance is calculated by taking into account allowances stored in a performance database of the aircraft. Also, the descent time is calculated based on a wind velocity at the each of the two reference points. The cruise time for the cruise distance is calculated based on the formula: cruise time=cruise distance/ground speed, where the ground speed is a sum of a true air speed (TAS) and a wind velocity at a cruise altitude. It can be noted that, the cruise time is calculated based on an assumption that an expected cruise flight of the aircraft for the cruise distance is carried out at an optimum mach based on a predicted gross weight of the aircraft and an effect of wind at the EDP.

Figure 6:
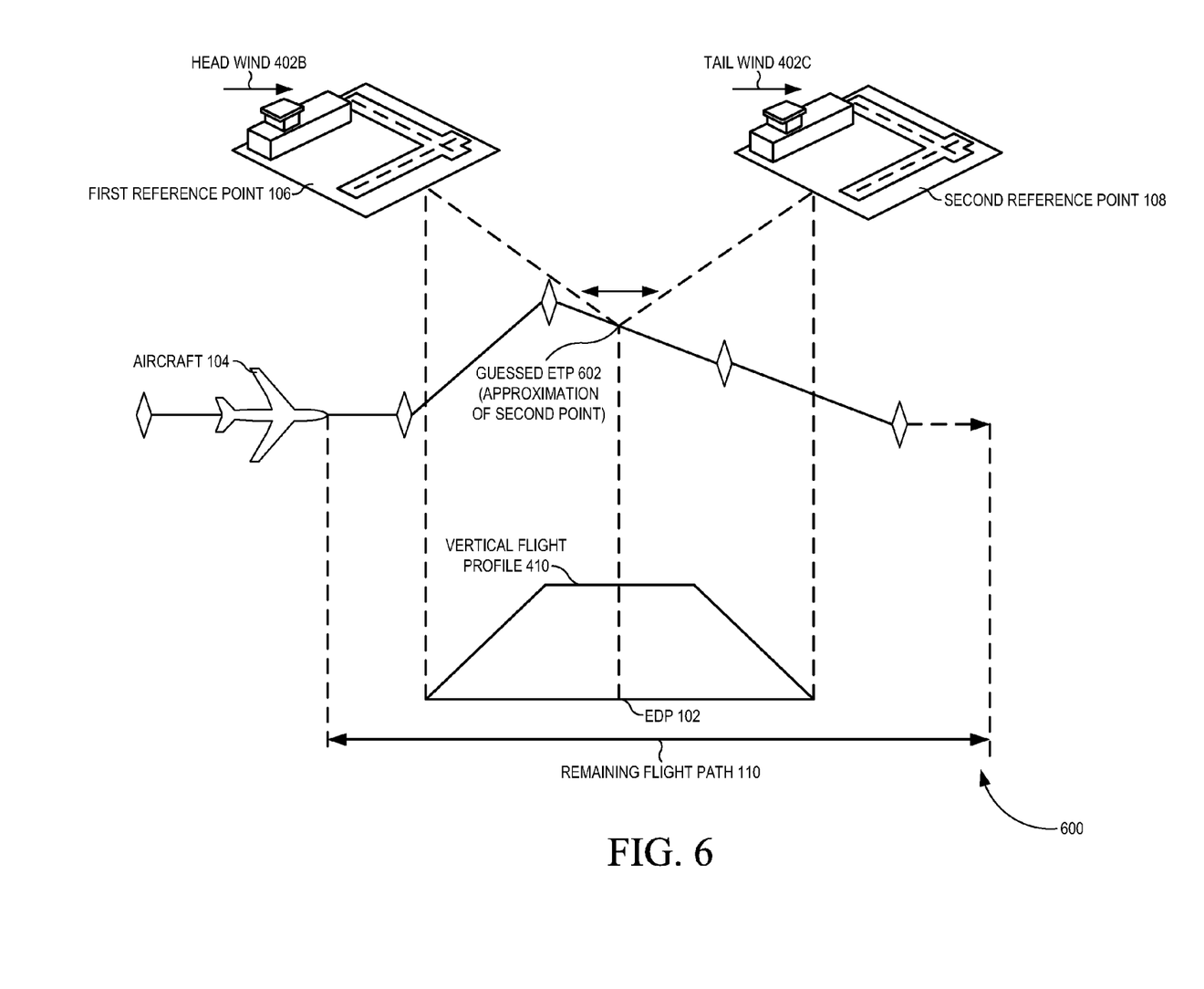
FIG. 6 illustrates an exemplary schematic representation illustrating computation of flight time from a guessed equi-time point (ETP) to each reference point, according to an embodiment of the invention.

FIG. 6 illustrates an exemplary schematic representation 600 illustrating computation of flight time from a guessed ETP 602 to each reference point, according to an embodiment of the invention. Particularly, FIG. 6 illustrates generation of the guessed ETP 602 by locating a point (by approximation) on the remaining flight path 110 based on the EDP 102. According to an embodiment of the present invention, a first expected flight time taken from the guessed ETP 602 to the first reference point 106 is computed. Then, a second expected flight time taken from the guessed ETP 602 to the second reference point 108 is computed. It is appreciated that the first expected flight time and the second expected flight time are computed based on performance data stored in a performance database of the aircraft 104. It is also appreciated that the first expected flight time and the second expected flight time are computed based on the vertical flight profile 410 flying a great circle distance, as described in FIG. 4.

Further, a difference between the first expected flight time and the second expected flight time is determined. Then, it is determined whether the time difference is less than a threshold value (e.g., one minute). If the time difference is found to be less than the threshold value, the guessed ETP 602 is determined as the ETP for the aircraft 104 from the first reference point 106 and the second reference point 108.

However, if the time difference is found to be greater than the threshold value, then the guessed ETP 602 is shifted by moving along the remaining flight path 110 by a step to determine the ETP. The step may be based on a vector difference between a first wind velocity (e.g., the head wind 402B) at the first reference point 106 in nautical miles per hour and a second wind velocity (e.g., the tail wind 402C) at the second reference point 108 in nautical miles per hour multiplied by 0.1 hour.

In one embodiment, the guessed ETP 602 is moved along the remaining flight path 110 toward the first reference point 106. This is when the first expected flight time to the first reference point 106 is greater than the second expected flight time to the second reference point 108 for more than the threshold value. In an alternate embodiment, the guessed ETP 602 is moved along the remaining flight path 110 toward the second reference point 108. This is when the second expected flight time to the second reference point 108 is greater than the first expected flight time to the first reference point 106 for more than the threshold value. It should be noted that, steps for computing the first expected flight time and the second expected flight time as well as for moving the guessed ETP 602 may be repeatedly performed until the difference between the first expected flight time and the second expected flight time becomes less than the threshold value. Thus, when the time difference is found to be less than the threshold value, the guessed ETP 602 is determined as the ETP, as illustrated in FIG. 7.

Figure 7:
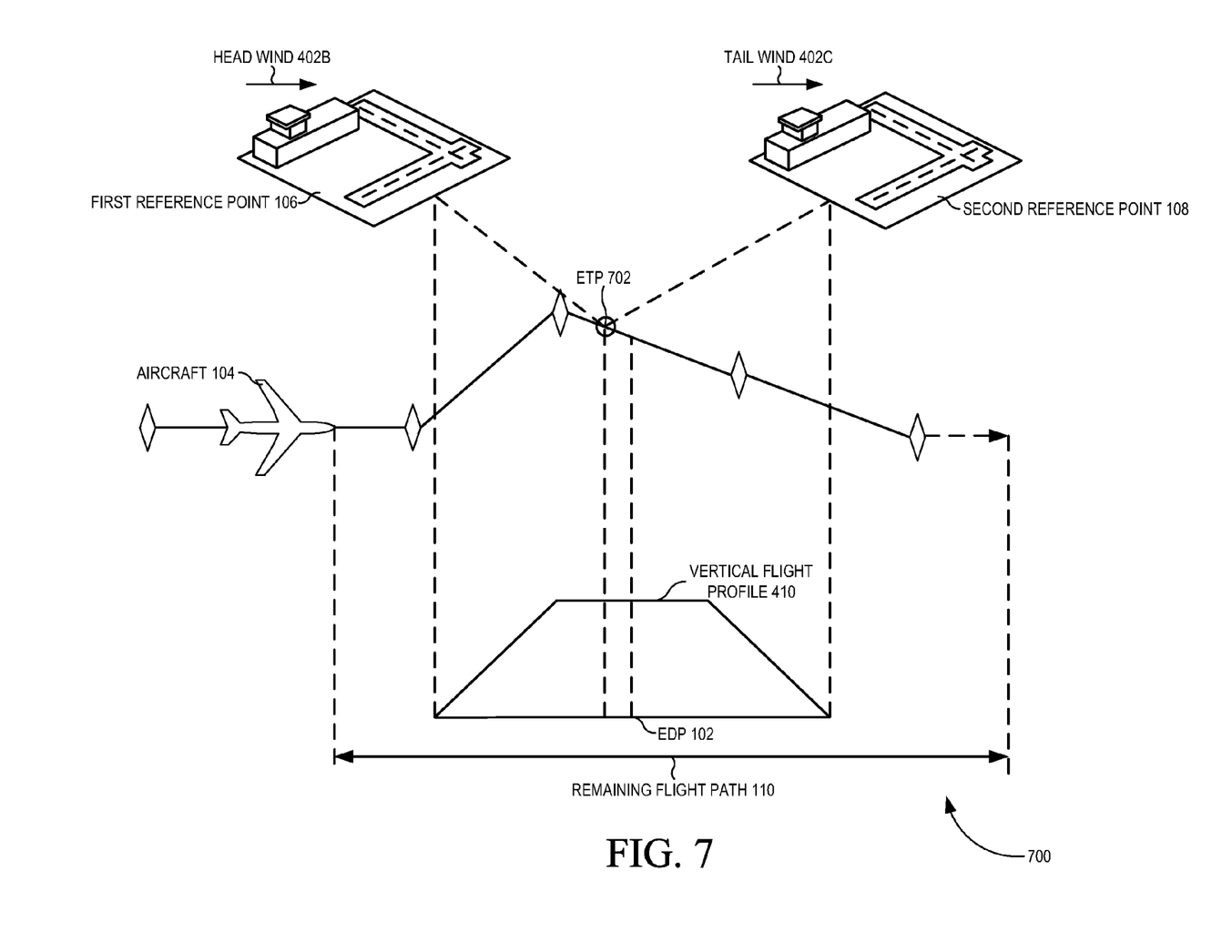
FIG. 7 illustrates an exemplary schematic representation illustrating determination of an ETP, according to an embodiment of the invention.

FIG. 7 illustrates an exemplary schematic representation 700 illustrating determination of an ETP 702, according to an embodiment of the invention. As illustrated, a point on the remaining flight path 110 of the aircraft 104 is determined as the ETP 702 when the time difference between the first expected flight time from the ETP 702 to the first reference point 106 and the second expected flight time from the ETP 702 to the second reference point 108 is less than the threshold value. In the example embodiment illustrated in FIG. 7, the ETP 702 is determined by moving the guessed ETP 602 toward the first reference point 106. Accordingly, as illustrated in FIG. 7, the ETP 702 is located closer to the first reference point 106 than to the second reference point 108, and the ETP 702 does not coincide with the EDP 102.

Figure 8:
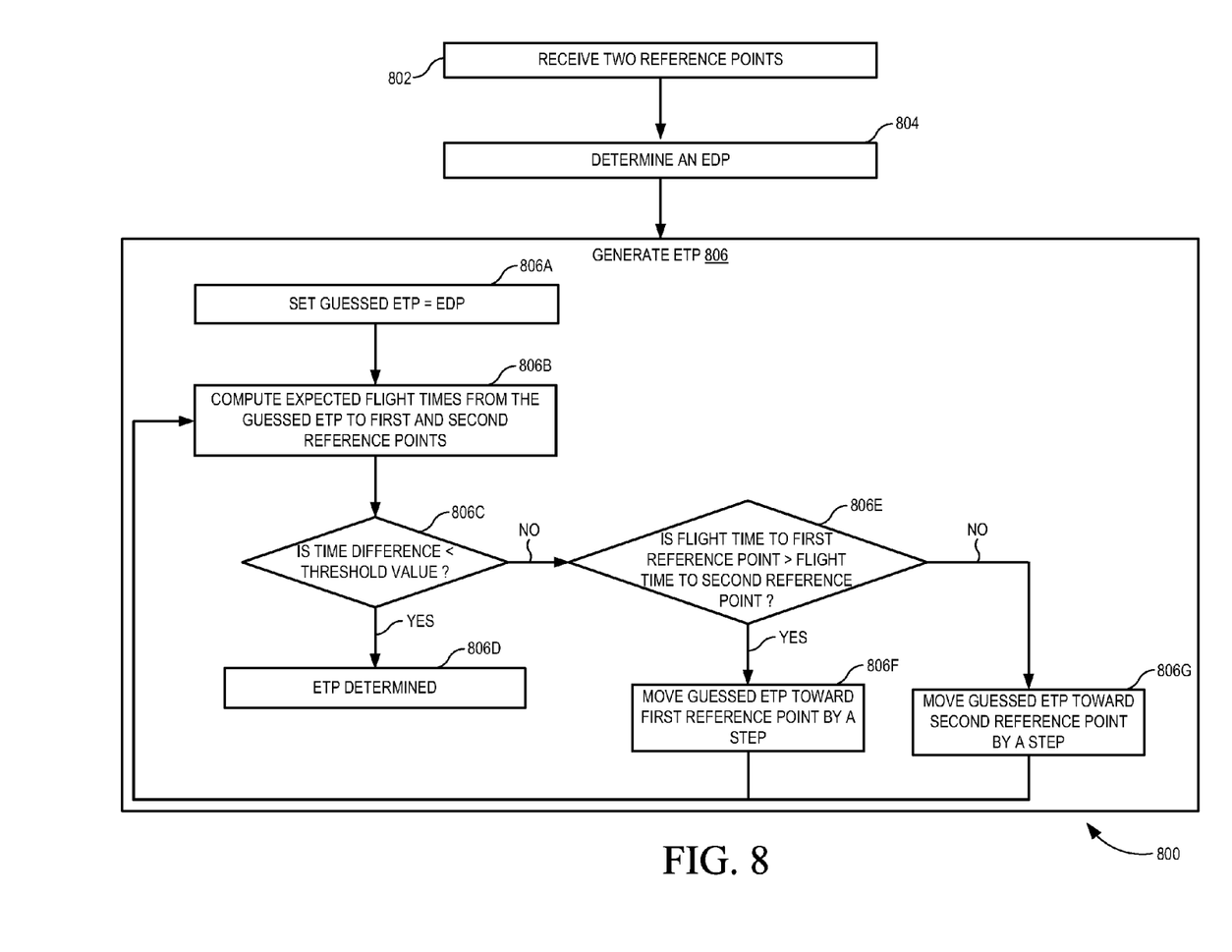
FIG. 8 illustrates a process flowchart of an exemplary method of an FMS of an aircraft for computing an ETP, according to an embodiment of the invention.

FIG. 8 illustrates a process flowchart 800 of an exemplary method of an FMS of an aircraft for computing an ETP for the aircraft, according to an embodiment of the invention. In step 802, two reference points (hereinafter referred to as a first reference point and a second reference point) are received for landing the aircraft upon occurrence of an emergency. In step 804, an EDP for the aircraft is determined by locating a first point on a remaining flight path of the aircraft. The first point on the remaining flight path is equidistant from the first reference point and the second reference point. It is appreciated that the EDP for the aircraft is determined using the method described in FIG. 3. In step 806, an ETP for the aircraft is generated by locating a second point on the remaining flight path of the aircraft. The steps involved in generating the ETP are described in steps 806A-G.

In step 806A, the EDP for the aircraft is set as a guessed ETP for the aircraft. In one example embodiment, the guessed ETP is generated by approximating the second point on the remaining flight path based on the EDP. In step 806B, a first expected flight time from the guessed ETP to the first reference point is computed. Also, in step 806B, a second expected flight time from the guessed ETP to the second reference point is computed. In step 806C, it is determined whether a difference between the first expected flight time and the second expected flight time is found to be less than a threshold value (e.g., one minute). If the time difference is found to be less than the threshold value, then the guessed ETP is determined as an ETP for the aircraft in step 806D.

If the time difference is found to be greater than the threshold value, then the process 800 performs step 806E. In step 806E, it is determined whether the first expected flight time is greater than the second expected flight time for more than the threshold value. If the first expected flight time is found to be greater than the second expected flight time for more than the threshold value, then the process 800 performs step 806F. In step 806F, the guessed ETP is moved along the remaining flight path toward the first reference point by a step. In one example embodiment, the step is based on a vector difference between a first wind velocity at the first reference point in nautical miles per hour and a second wind velocity at the second reference point in nautical miles per hour multiplied by 0.1 hour.

If the second expected flight time is greater than the first expected flight time for more than the threshold value, then the process 800 performs step 806G. In step 806G, the guessed ETP is moved along the remaining flight path toward the second reference point by the step. Further, upon performing step 806F or 806G, the process 800 repeats the step 806B to compute a first expected flight time and a second expected flight time from the new guessed ETP to the first reference point and the second reference point respectively. It is appreciated that, steps 806C, 806E, and 806F or 806G are repeated until the ETP is determined. It is also appreciated that, the steps 802-806 may use mathematical formulas described in FIG. 2 and FIG. 4 to generate the ETP on the remaining flight path of the aircraft.

Figure 9:
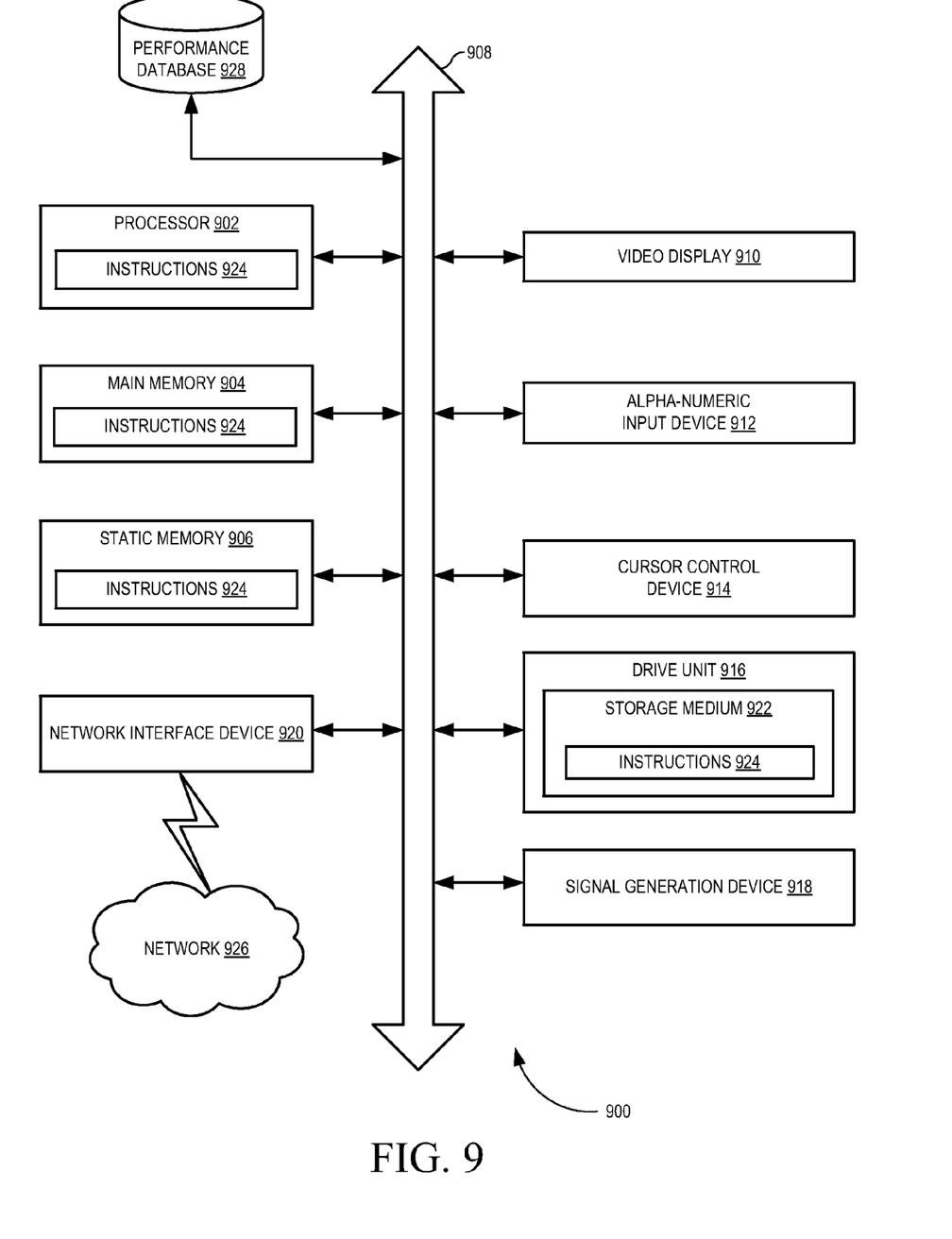
FIG. 9 illustrates a diagrammatic system view of a data processing system of an FMS in which any of the embodiments disclosed herein may be performed, according to an embodiment of the invention.

FIG. 9 illustrates a diagrammatic system view 900 of a data processing system of an FMS in which any of the embodiments disclosed herein may be performed, according to an embodiment of the invention. Particularly, the diagrammatic system view 900 of FIG. 9 illustrates a processor 902, a main memory 904, a static memory 906, a bus 908, a video display 910, an alpha-numeric input device 912, a cursor control device 914, a drive unit 916, a signal generation device 918, a network interface device 920, a storage medium 922, instructions 924, a network 926 and a performance database 928.

The diagrammatic system view 900 may indicate a data processing system of the FMS of the aircraft (e.g., the aircraft 104 of FIGS. 1, 2, 4, 6 and 7) in which one or more operations disclosed herein are performed. The processor 902 may be a microprocessor, a state machine, an application specific integrated circuit, a field programmable gate array, etc. The main memory 904 may be a dynamic random access memory and/or a primary memory of the FMS. The static memory 906 may be a hard drive, a flash drive, and/or other memory information associated with the data processing system.

The bus 908 may be an interconnection between various circuits and/or structures of the data processing system. The video display 910 may provide graphical representation of information on the data processing system. The alpha-numeric input device 912 may be a keypad, keyboard and/or any other input device of text (e.g., a special device to aid the physically handicapped). The cursor control device 914 may be a pointing device such as a mouse. The drive unit 916 may be a hard drive, a flash system, and/or other longer term storage subsystem.

The signal generation device 918 may be a BIOS and/or a functional operating system of the data processing system. The network interface device 920 may perform interface functions (e.g., code conversion, protocol conversion, and/or buffering) required for communications to and from the network 926 between a number of independent devices (e.g., of varying protocols). The storage medium 922 may provide instructions on which any of the methods disclosed herein may be performed. The instructions 924 may provide source code and/or data code to the processor 902 to enable any one or more operations disclosed herein. The performance database 928 may be a database coupled to the processor 902 and is configured to store data associated with the aircraft (e.g., performance data used to calculate expected flight times of the aircraft).

In one embodiment, the storage medium 922 has instructions 924, that when executed by a computing platform of the FMS of the aircraft, result in execution of a method for generating an ETP for an emergency landing of the aircraft. The method includes receiving at least two reference points (e.g., the first reference point 106 and a second reference point 108) for landing the aircraft upon an occurrence of an emergency. The method also includes determining an EDP for the aircraft by locating a first point on the remaining flight path of the aircraft which is equidistant from the at least two reference points. Then, the method includes generating an ETP for the aircraft by locating a second point on the remaining flight path of the aircraft such that a time difference between any two of expected flight times of the aircraft from the second point to the at least two reference points is less than a threshold value, where an approximation of the second point is initially based on the EDP.

In one example embodiment, for generating the ETP for the aircraft, the storage medium 922 may have instructions 924 to compute a first expected flight time taken from the approximation of the second point to the first reference point and compute a second expected flight time taken from the approximation of the second point to the second reference point. Further, the storage medium 922 may have instructions 924 to determine the second point as the ETP when a difference between the first expected flight time and the second expected flight time is less than the threshold value.

In another example embodiment, for generating the ETP for the aircraft, the storage medium 922 may have instructions 924 to (a) compute a first expected flight time taken from the approximation of the second point to the first reference point, (b) compute a second expected flight time taken from the approximation of the second point to the second reference point, and (c) shift the approximation of the second point when a difference between the first expected flight time and the second expected flight time is greater than the threshold value.

Further, the storage medium 922 may have instructions 924 to shift the approximation of the second reference point by moving the approximation of the second point along the remaining flight path toward the first reference point by a step when the first expected flight time to the first reference point is greater than the second expected flight time to the second reference point for more than the threshold value. In one embodiment, the step is based on a vector difference between a first wind velocity at the first reference point in nautical miles per hour and a second wind velocity at the second reference point in nautical miles per hour multiplied by 0.1 hour.

Furthermore, the storage medium 922 may have instructions to shift the approximation of the second point by moving the approximation of the second point along the remaining flight path toward the second point by the step when the second expected flight time to the second point is greater than the first expected flight time to the first reference point. Moreover, the storage medium 922 may have instructions to repeat steps (a), (b), and (c) until the time difference is less than the threshold value. Thus, when the time difference is less than the threshold value, the storage medium 922 may have instructions to determine the second point as the ETP.

In another embodiment, the data processing system of the FMS of the aircraft for generating an ETP for an emergency landing of the aircraft includes the main memory 904 coupled to the processor 902 which has instructions 922 stored therein, that when executed by the processor 902 causes the processor 902 to perform the method described above.

In addition, it will be appreciated that the various operations, processes, and methods disclosed herein may be embodied in a machine-readable medium and/or a machine accessible medium compatible with a data processing system, and may be performed in any order (e.g., including using means for achieving the various operations). Accordingly, the specification and drawings are to be regarded in an illustrative rather than a restrictive sense.

What is claimed is:

1. A method of a flight management system (FMS) of an aircraft for generating an equi-time point (ETP) for an emergency landing of the aircraft, comprising:
   receiving, by a processor, at least two reference points for landing the aircraft upon an occurrence of an emergency;
   determining, by the processor, an equi-distance point (EDP) for the aircraft by locating a first point on a remaining flight path of the aircraft which is equidistant from the at least two reference points; and
   generating, by the processor, an equi-time point (ETP) for the aircraft by locating a second point on the remaining flight path of the aircraft, wherein a time difference between any two of expected flight times of the aircraft from the second point to the at least two reference points is less than a threshold value, and wherein an approximation of the second point is initially based on the equi-distance point.

2. The method of claim 1, wherein the remaining flight path for the aircraft is determined based on a current location of the aircraft and a flight plan serviced by the flight management system.

3. The method of claim 1, wherein the at least two reference points comprises a first reference point and a second reference point.

4. The method of claim 3, wherein the generating the equi-time point of the aircraft comprises:
   computing a first expected flight time from the approximation of the second point to the first reference point;
   computing a second expected flight time taken from the approximation of the second point to the second reference point; and
   determining the second point as the equi-time point when a difference between the first expected flight time and the second expected flight time is less than the threshold value.

5. The method of claim 3, wherein the generating the equi-time point of the aircraft comprises:
   (a) computing a first expected flight time from the approximation of the second point to the first reference point;
   (b) computing a second expected flight time taken from the approximation of the second point to the second reference point; and
   (c) shifting the approximation of the second point when a difference between the first expected flight time and the second expected flight time is greater than the threshold value.

6. The method of claim 5, wherein the generating the equi-time point of the aircraft further comprises:
   repeating steps (a), (b), and (c) until the difference between the first expected flight time and the second expected flight time is less than the threshold value; and
   determining the second point as the equi-time point.

7. The method of claim 5, wherein the shifting the approximation of the second point comprises moving the approximation of the second point along the remaining flight path toward the first reference point by a step when the first expected flight time to the first reference point is greater than the second expected flight time to the second reference point for more than the threshold value.

8. The method of claim 5, wherein the shifting the approximation of the second point comprises moving the approximation of the second point along the remaining flight path toward the second reference point by a step when the second expected flight time to the second reference point is greater than the first expected flight time to the first reference point for more than the threshold value.

9. The method of claim 7 or 8, wherein the step is based on a vector difference between a first wind velocity at the first reference point in nautical miles per hour and a second wind velocity in nautical miles per hour at the second reference point multiplied by 0.1 hour.

10. The method of claim 1, wherein the threshold value comprises one minute.

11. An article, comprising:
   a non-transitory computer readable storage medium having instructions, that when executed by a computing platform of a flight management system (FMS) of an aircraft, result in execution of a method for generating an equi-time point (ETP) for an emergency landing of the aircraft, comprising:
      receiving at least two reference points for landing the aircraft upon an occurrence of an emergency;
      determining an equi-distance point (EDP) for the aircraft by locating a first point on a remaining flight path of the aircraft which is equidistant from the at least two reference points; and
      generating an equi-time point (ETP) for the aircraft by locating a second point on the remaining flight path of the aircraft, wherein a time difference between any two of expected flight times of the aircraft from the second point to the at least two reference points is less than a threshold value, and wherein an approximation of the second point is initially based on the equi-distance point.

12. The article of claim 11, wherein the at least two reference points comprises a first reference point and a second reference point.

13. The article of claim 12, wherein the generating the equi-time point of the aircraft comprises:
   computing a first expected flight time from the approximation of the second point to the first reference point;
   computing a second expected flight time taken from the approximation of the second point to the second reference point; and
   determining the second point as the equi-time point when a difference between the first expected flight time and the second expected flight time is less than the threshold value.

14. The article of claim 12, wherein the generating the equi-time point of the aircraft comprises:
   (a) computing a first expected flight time from the approximation of the second point to the first reference point;
   (b) computing a second expected flight time taken from the approximation of the second point to the second reference point; and
   (c) shifting the approximation of the second point when a difference between the first expected flight time and the second expected flight time is greater than the threshold value.

15. The article of claim 14, wherein the generating the equi-time point of the aircraft further comprises:
   repeating steps (a), (b), and (c) until the difference between the first expected flight time and the second expected flight time is less than the threshold value; and
   determining the second point as the equi-time point.

16. The article of claim 14, wherein the shifting the approximation of the second point comprises moving the approximation of the second point along the remaining flight path toward the first reference point by a step when the first expected flight time to the first reference point is greater than the second expected flight time to the second reference point for more than the threshold value.

17. The article of claim 14, wherein the shifting the approximation of the second point comprises moving the approximation of the second point along the remaining flight path toward the second reference point by a step when the second expected flight time to the second reference point is greater than the first expected flight time to the first reference point for more than the threshold value.

18. The article of claim 16 or 17, wherein the step is based on a vector difference between a first wind velocity at the first reference point in nautical miles per hour and a second wind velocity in nautical miles per hour at the second reference point multiplied by 0.1 hour.

19. A system of a flight management system (FMS) of an aircraft for generating an equi-time point (ETP) for an emergency landing of the aircraft, comprising:
 a processor; and
 a memory coupled to the processor and configured for storing a set of instructions, when executed by the processor, causes the processor to perform a method comprising:
  receiving at least two reference points for landing the aircraft upon an occurrence of an emergency;
  determining an equi-distance point (EDP) for the aircraft by locating a first point on a remaining flight path of the aircraft which is equidistant from the at least two reference points; and
  generating an equi-time point (ETP) for the aircraft by locating a second point on the remaining flight path of the aircraft, wherein a time difference between any two of expected flight times of the aircraft from the second point to the at least two reference points is less than a threshold value, and wherein an approximation of the second point is initially based on the equi-distance point.

20. The system of claim 19, further comprising a performance database coupled to the processor for storing performance data used to calculate the expected flight times of the aircraft.

* * * * *